(12) United States Patent
Freed et al.

(10) Patent No.: US 9,480,673 B2
(45) Date of Patent: Nov. 1, 2016

(54) COMPOSITION AND METHOD FOR TREATING NEURODEGENERATIVE DISEASE

(71) Applicant: The Regents of the University of Colorado, a body corporate, Denver, CO (US)

(72) Inventors: Curt R. Freed, Denver, CO (US); Wenbo Zhou, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 130 days.

(21) Appl. No.: 14/388,929

(22) PCT Filed: Mar. 28, 2013

(86) PCT No.: PCT/US2013/034501
§ 371 (c)(1),
(2) Date: Sep. 29, 2014

(87) PCT Pub. No.: WO2013/149091
PCT Pub. Date: Oct. 3, 2013

(65) Prior Publication Data
US 2015/0087703 A1     Mar. 26, 2015

Related U.S. Application Data
(60) Provisional application No. 61/617,055, filed on Mar. 29, 2012.

(51) Int. Cl.
| | |
|---|---|
| *A61K 31/19* | (2006.01) |
| *A61K 31/192* | (2006.01) |
| *A61K 31/21* | (2006.01) |
| *A61K 31/216* | (2006.01) |

(52) U.S. Cl.
CPC ............ *A61K 31/216* (2013.01); *A61K 31/19* (2013.01); *A61K 31/192* (2013.01); *A61K 31/21* (2013.01)

(58) Field of Classification Search
CPC .... A61K 31/19; A61K 31/192; A61K 31/21; A61K 31/216
See application file for complete search history.

(56) References Cited

U.S. PATENT DOCUMENTS

2011/0027251 A1    2/2011    Frechilla et al.

OTHER PUBLICATIONS

Adams et al., "Characterization and Transplantation of Two Neuronal Cell Lines with Dopaminergic Properties," (1996) Neurochem Res 21(5), 619-627.
Allam et al., "Parkinson's disease risk factors: genetic environmental, or both?" (2005) Neurol Res 27(2), 206-208.
Alves Da Costa et al., "α—Synuclein Lowers p53-dependent Apoptotic Response of Neuronal Cells," (2002) J Biol Chem 277(52), 50980-50984.
Andreassi et al., Phenylbutyrate increases SMN expression in vitro relevance for treatment of spinal muscular atrophy, (2004) Eur J Hum Genet 12(1), 59-65.
Baba et al., "Aggregation of α-Synuclein in Lewy Bodies of Sporadic Parkinson's Disease and Dementia with Lewy Bodies," (1998) Am J Pathol 152(4), 879-884.
Bonifati et al "Mutations in the DJ-1 Gene Associated with Autosomal Recessive Early-Onset Parkinsonism," (2003) Science 299(5604), 256-259.
Bonifati, "Genetics of Parkinson's disease," (2005) Minerva Med 96(3), 175-186.
Brahe et al., "Phenylbutyrate increases SMN gene expression in spinal muscular atrophy patients," (2005) Eur JHum Genet 13(2), 256-259.
Brown et al., "Neurodegenerative Diseases: An Overview of Environmental Risk Factors," (2005) Environ Health Perspect., 113(9), 1250-1256.
Canet-Aviles et al., "The Parkinson's disease protein DJ-1 is neuroprotective due to cysteine-sulfinic acid-driven mitochondrial localization," (2004) Proc Natl Acad Sci U S A 101(24), 9103-9108.
Clark et al., "Analysis of an Early-Onset Parkinson's Disease Cohort for DJ-1 Mutations," (2004) Mov Disord 19(7), 796-800.
Clements et al., "DJ-1, a cancer- and Parkinson's disease-associated protein, stabilizes the antioxidant transcriptional master regulator Nrf2," (2006) Proc Natl Acad Sci USA 103(41), 15091-15096.
Conway et al., "Accelerated in vitro fibril formation by a mutant α-synuclein linked to early-onset Parkinson disease," (1998) Nat Med 4(1 1), 1318-1320.
Cookson et.al., "Parkinson's disease: insights from pathways," (2010) Hum Mol Genet 19(RI), R21-27.
Cookson, "The Biochemistry of Parkinson's Disease," (2005) Annu Rev Biochem 74, 29-52.
Cudkowicz et al., "Phase 2 study of sodium phenylbutyrate in ALS," (2009) Amyotroph Lateral Soler, 10:99-106.
Gardian et al, "Neuroprotective Effects of Phenylbutyrate in the N171-82Q Transgenic Mouse Model of Huntington's Disease," (2005) J Biol Chem 280(1), 556-563.
Gardian et al., "Neuroprotective Effects of Phenylbutyrate Against MPTP Neurotoxicity," (2004) Neuromolecular Med 5(3), 235-241.
Gondcaille ct al., "Phenylbutyrate up-regulates the adrenoleukodystrophy-related gene as a nonclassical peroxisome proliferator," (2005) J Cell Biol 169(1), 93-104.
Hague et al., "Early-Onset Parkinson's Disease Caused by a Compound Heterozygous DJ-1 Mutation," (2003) Ann Neurol 54(2), 271-274.
Hashimoto et al., Transgenic Models of α-Synuclein Pathology Past, Present, and Future, (2003) Ann N Y Acad Sci 991, 171-188.
Hogarth et al., "Sodium Phenylbutyrate in Huntington's Disease: A Dose-Finding Study," (2007) Mov Disord 22(13), 1962-1964.
Huang et al., "Genetic contributions to Parkinson's disease," (2004) Brain Res Brain Res Rev 46(1), 44-70.

(Continued)

*Primary Examiner* — Yong Chong
(74) *Attorney, Agent, or Firm* — Perkins Coie LLP

(57) ABSTRACT

The present invention provides a method and composition for treating a neurodegenerative disease. In particular, the present invention provides a method and composition to increase DJ-1 gene expression or DJ-1 protein activity to treat a neurodegenerative disease.

4 Claims, 11 Drawing Sheets

(56) References Cited

OTHER PUBLICATIONS

Ibanez et al., "Screening for DJ-1 mutations in early onset autosomal recessive parkinsonism," (2003) Neurology 61(10), 1429-1431.
Inden et al., "Neurodegeneration of mouse nigrostriatal dopaminergic system induced by repeated oral administration of rotenone is prevented by 4-phenylbutyrate, a chemical chaperone," (2007) J Neurochem 101(6), 1491-1504.
Irrcher et al., "Loss of the Parkinson's disease-linked gene DJ-1 perturbs mitochondrial dyanmics," (2010) Hum Mol Genet 19(19), 3734-3746.
Junn et al., "Mitochondrial Localization of DJ-1 Leads to Enhanced Neuroprotection," (2009) J Neurosci Res 87(1), 123-129.
Kaul et al., "Wild-type α-synuclein interacts with pro-apoptotic proteins PKCδ and BAD to protect dopaminergic neuronal cells against MPP+-induced apoptotic cell death," (2005) Brain Res. Mol Brain Res 139(1), 137-152.
Kim et al., "Histone deacetylase inhibitor apicidin induces cyclin E expression through Sp1 sites," (2006) Biochem Biophys Res Commun 342(4), 1168-1173.
Kim et al., "Hypersensitivity of DJ-1-deficient mice to 1-methyl-4-phenyl-1,2,3,6-tetrahydropyrindine (MPTP) and oxidative stress," (2005) Proc Natl Acad Sci U S A 102(14), 5215-5220.
Kim et al., "Sodium butyrate sensitizes TRAIL-mediated apoptosis by induction of transcription from the DR5 gene promoter through Sp1 sites in colon cancer cells," (2004) Carcinogenesis 25(10), 1813-1820.
Kruger et al., "Ala30Pro mutation in the gene encoding α-synuclein in Parkinson's disease," (1998) Nat Genet 18(2), 106-108.
Minamiyama et al., "Sodium butyrate ameliorates phenotypic expression in a transgenic mouse model of spinal and bulbar muscular atrophy," (2004) Hum Mol Genet 13(11), 1183-1192.
Morris, "Genetics of Parkinson's disease," (2005) Ann Med 37(2), 86-96.
Narhi et al., "Both Familial Parkinson's Disease Mutations Accelerate α-Synuclein Aggregation,"(1999) J Biol Chem 274(14), 9843-9846.
Ono et al., "A chemical chaperon sodium 4-phenylbutyric acid, attenuates the pathogenic potency in human α-synuclein A30P + A53T transgenic mice," (2009) Parkinsonism Related Disord 15:649-654.
Papp et al., "Chemical Chaperones: Mechanisms of action and Potential Use," (2006) Handb Exp Pharmacol (172), 405-416.
Perlmutter, "Chemical Chaperones: A Pharmacological Strategy for Disorders of Protein Folding and Trafficking," (2002) Pediatr Res 52(6), 832-836.
Polymeropoulos et al., "Mutation in the α-Synuclein Gene Identified in Families with Parkinson's Disease," (1997) Science 276(5321), 2045-2047.
Ryu et al., "Sodium phenylbutyrate prolongs survival and regulates expression of anti-apoptotic genes in transgenic amyotrophic lateral sclerosis mice," (2005) J Neurochcm 93(5), 1087-1098.
Shendelman et al., "DJ-1 is a Redox-Dependent Molecular Chaperone That Inhibits α-Synuclein Aggregate Formation," (2004) PLoS Biol 2(11), e362.
Spillantini et al., "α-Synuclein in Lewy Bodies," (1997) Nature 388(6645), 839-840.
Taira et al., "DJ-1 has a role in antioxidative stress to prevent cell death," (2004) EMBO Rep 5(2), 213-218.
Taira et al., "Molecular cloning of human and mouse DJ-1 genes and identification of Sp1-dependent activation of the human DJ-1 promoter," (2001) Gene 263(1-2), 285-292.
Thomas et al., "DJ-1 acts in parallel to the PINK1/parkin pathway to control mitochondrial function and autophagy," (2010) Hum Mol Genet.
Tremolizzo et al., "Valproate and HDAC Inhibition: A new epigenetic strategy to mitigate phenotypic severity in ALS?" (2005) Amyotroph Lateral Soler Other Motor Neuron Disord 6(3), 185-186.
Trojanowski et al., "Aggregation of Neurofilament and α-Synuclein Proteins in Lewy Bodies," (1998) Arch Neurol 55(2), 51-152.
Wood et al., "α-Synuclein Fibrillogenesis Is Nucleation-dependent," (1999) J Biol Chem 274(28), 19509-19512.
Yam et al., "Sodium 4-Phenylbutyrate Acts as a Chemical Chaperone on Misfolded Myocilin to Rescue Cells from Endoplasmic Reticulum Stress and Apoptosis," (2007) Invest Ophthalmol Vis Sci 48(4), 1683-1690.
Ying et al., "Sodium Butyrate Ameliorates Histone Hypoacetylation and Neurodegenerative Phenotypes in a Mouse Model for DRPLA," (2006) J Biol Chem 281(18), 12580-12586.
Yokota et al., "Histone deacetylase inhibitors activate INK4d gene through Sp1 site in its promoter," (2004) Oncogene 23(31), 5340-5349.
Zarranz et al., "The New Mutation, E46K, of α-Synuclein Causes Parkinson and Lewy Body Dementia," (2004) Ann Neurol 55(2), 164-173.
Zhou et al., "Overexpression of human α-synuclein causes dopamine neuron death in primary human mesencephalic culture," (2002) Brain Res 926(1-2), 42-50.
Zhou et al., "Overexpression of human α-synuclein causes dopamine neuron death in rat primary culture and immortalized mesencephalon-derived cells," (2000) Brain Res 866(1-2), 33-43.
Zhou et al., "Phenylbutyrate Upregulates DJ-1 and Protects Neurons in Cell Culture and in Animal Models of Parkinson Disease," JBC Papers in Press (2011) Manuscript M110.211029.
Zhou et al., "The Oxidation State of DJ-1 Regulates its Chaperone Activity Toward α-Synuclein," (2006) J Mol Biol 356(4), 1036-1048.
Zhou et al., "Transgenic Mice Overexpressing Tyrosine-to-Cysteine Mutant Human α-Synuclein,"(2008) J Biol Chem 283(15), 9863-9870.
Zhou et al., "Tyrosine-to-Cysteine Modification of Human α-Synuclein Enhances Protein Aggregation and Cellular Toxicity," (2004) J Biol Chem 279(11), 10128-10135.
Zhou et al., "DJ-1 Up-regulates Glutathione Synthesis during Oxidative Stress and Inhibits A53T α-Synuclein Toxicity," (2005) J. Biol. Chem. 280(52), 43150-43158.

COMPOSITION AND METHOD FOR TREATING NEURODEGENERATIVE DISEASE

CROSS-REFERENCE TO RELATED APPLICATIONS

This application claims the priority benefit of U.S. Provisional Application No. 61/617,055, filed Mar. 29, 2012, which is incorporated herein by reference in its entirety.

FIELD OF THE INVENTION

The present invention relates to compositions and methods for treating a neurodegenerative disease. In particular, the present invention relates to increasing DJ-1 gene expression or DJ-1 protein activity to treat a neurodegenerative disease.

BACKGROUND OF THE INVENTION

Neurodegenerative diseases such as Parkinson's disease, Alzheimer's disease and Huntington's disease are caused by the death of neurons. As used herein, the term "neurodegenerative" refers to the loss or death of neurons causing the disease. Typically, neurodegenerative diseases are characterized by a slow onset and chronic progression. In a neurodegenerative disease, a particular part of the brain, spinal cord, or peripheral nerve functionally fails and the neurons of the dysfunctional region die. Neurodegenerative diseases are often categorized by whether they initially affect cognition, movement, strength, coordination, sensation, or autonomic control. However, it is not uncommon for patients to be presented with symptoms and signs to more than one system. While it is possible that involvement of several systems can occur concomitantly, typically by the time the patient has functionally declined enough to seek medical attention multiple systems have become involved. Diagnosing neurodegenerative diseases can prove particularly intimidating to clinicians, because many times the diagnosis cannot be critically "confirmed" by a simple test.

The prevalence of neurodegenerative diseases has increased drastically. In fact, it is estimated that currently Alzheimer's disease is now the sixth leading cause of death in the U.S.

Accordingly, there is an urgent need for effective treatments of neurodegenerative diseases.

SUMMARY OF THE INVENTION

Some aspects of the invention are based on the discovery by the present inventors that increasing DJ-1 gene expression or increasing DJ-1 protein activity can be beneficial to neurons. In particular, it has been discovered by the present inventors that increasing DJ-1 gene expression or DJ-1 protein activity protects dopamine producing neurons from apoptosis. Accordingly, in some aspects of the invention provides a method for treating a neurodegenerative disease in a subject, such method typically comprising administering to a subject in need of such a treatment a composition comprising a compound that increases DJ-1 gene expression or DJ-1 protein activity. The term "treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

In some embodiments, the compound increases DJ-1 gene expression by at least 50%, typically at least 100%, often at least 200%, and most often at least 300%.

Yet in other embodiments, the compound is administered to the subject no more than 10 units, typically no more than 5 units and often no more than 3 units, per day.

Exemplary neurodegenerative diseases that can be treated by methods and/or compositions of the invention include neurodegenerative diseases associated with a build-up of particular proteins such as, but not limited to, $\alpha$-synuclein or $\beta$-amyloid including amyloid angiopathy. In general, any neurodegenerative diseases that are associated with abnormal accumulation or build-up of a protein within or near the neurons can be treated by methods and compositions disclosed herein. Some specific examples of neurodegenerative diseases that can be treated by methods and compositions of the invention include, but are not limited to, Parkinson's disease, Alzheimer's disease, Huntington's disease, Multiple System Atrophy, Progressive Supranuclear Palsy, Down syndrome, diffuse Lewy body disease, and amyotrophic lateral sclerosis.

Yet in other embodiments, the compound that can be used to treat a neurodegenerative disease is a histone deacetylase (HDAC) inhibitor.

In some embodiments, the compound that is used to treat a neurodegenerative disease upregulates DJ-1 gene expression. In other embodiments, the compound increases the activity of DJ-1 protein.

In one particular embodiment, the compound comprises phenylbutyric acid, butytric acid, a salt thereof, a prodrug thereof, or a derivative thereof. In another embodiments, the compound comprises phenylbutyrate or a prodrug thereof, or a derivative thereof. Still in another embodiment, the compound comprises phenylbutyrate glycerol.

Yet another aspect of the invention provides a method for treating a neurodegenerative disease in a subject in need of such a treatment. Such method generally includes increasing DJ-1 expression in the subject by administering a therapeutically effective amount of a compound that increases DJ-1 expression level by at least 50%, typically at least 100%, often at least 200%, and most often at least 300%. Increase in DJ-1 expression reduces the amount of neuron death. As used herein, the term "a therapeutically effective amount" means the amount of a compound that, when administered to a mammal for treating a disease, is sufficient to effect such treatment for the disease. It should be appreciated that the "therapeutically effective amount" will vary depending on the compound, the disease and its severity and the age, weight, etc., of the mammal to be treated.

Still another aspect of the invention provides a method for protecting dopamine neurons from a neurotoxic insult comprising administering a compound to increase DJ-1 expression in the dopamine neurons, thereby increasing survivability of said dopamine neurons. It should be appreciated that whether a particular compound or a composition can increase DJ-1 expression of DJ-1 protein activity can be readily determined by one skilled in the art having read the present disclosure.

DETAILED DESCRIPTION OF THE INVENTION

Figure 1:
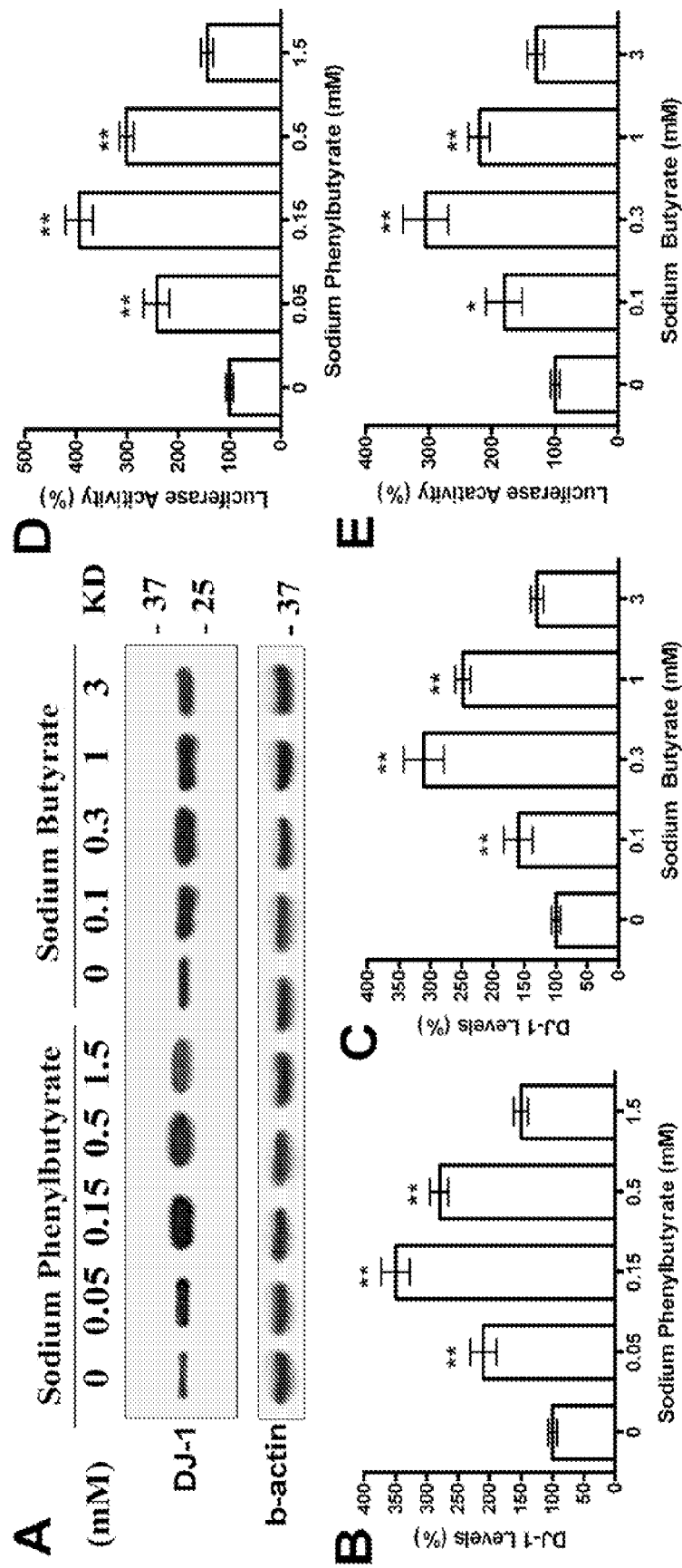
FIG. 1A is a western blot image showing sodium phenylbutyrate (PB) and sodium butyrate (SB) increases DJ-1 expression in N27 and HEK293 cells.
FIGS. 1B and 1C are quantitative data from Western blot images ($*p<0.05$, $**p<0.01$ compared to control, n=6) showing the amount of increase in DJ-1 expression in N27 and HEK293 cells by PB and SB.
FIGS. 1D and 1E are bar graphs showing the average luciferase activity ($*p<0.05$, $**p<0.01$ compared to control, n=6) in HEK293 reporter cells expressing human DJ-1 promoter-Luciferase that were treated with PB or SB at indicated doses for 48 hr.

Parkinson's disease is caused by the death of midbrain dopamine neurons due to a variety of factors including, but not limited to, oxidative stress, abnormal protein aggregation, and genetic predisposition. In 2003, Bonifati et al. found that a single amino acid mutation in the DJ-1 protein was associated with early-onset, autosomal recessive Parkinson's disease (PARK7). The mutation L166P prevents dimerization that is essential for the antioxidant and gene regulatory activity of the DJ-1 protein. Thus, the absence of normal DJ-1 protein causes Parkinson's disease.

Some aspects of the invention are based on the discovery by the present inventors that increasing the expression (i.e., overexpression) and/or the activity of DJ-1 protein can be an effective treatment for neurodegenerative diseases such as Parkinson's disease. It should be appreciated that when referring to overexpressing or increasing the activity of DJ-1 protein, the present disclosure refers to overexpressing or increasing the activity of non-mutant DJ-1 protein. The term "mutant DJ-1 protein" refers to a DJ-1 protein having a mutation that is associated with early-onset of neurodegenerative disease, such as autosomal recessive Parkinson's disease. Thus, the corollary term "normal DJ-1 protein" refers to any DJ-1 protein that is not associated with an early-onset of neurodegenerative disease. As used herein, the term "expression" refers to (1) the amount of transcription and/or translation of DJ-1 gene, (2) the amount of DJ-1 protein present in the subject or (3) both. To detect expression of a gene refers to the act of actively determining whether a gene is expressed or not. This can include determining whether the gene expression is upregulated as compared to untreated state. It should be appreciated that levels of other biomarkers such as any portion of DJ-1 protein, DJ-1 mRNA, DJ-1 gene expression, or ligand that can identify or correlate with the level of DJ-1 protein can be used to determine the amount of DJ-1 protein present in the subject.

Unless the context requires otherwise, the terms "baseline" or "control" refers to the level of DJ-1 protein expression in a subject without administration or in the absence of any compound or composition that increases DJ-1 expression.

Expression of the transcripts and/or proteins encoded by DJ-1 gene can be measured by any of a variety of known methods in the art. In general, the nucleic acid sequence of a nucleic acid molecule (e.g., DNA or RNA) in a patient sample can be detected by any suitable method or technique of measuring or detecting gene sequence or expression. Such methods include, but are not limited to, polymerase chain reaction (PCR), reverse transcriptase-PCR (RT-PCR), in situ PCR, quantitative PCR (q-PCR), in situ hybridization, Southern blot, Northern blot, sequence analysis, microarray analysis, detection of a reporter gene, or other DNA/RNA hybridization platforms. For RNA expression, typical methods include, but are not limited to: extraction of cellular mRNA and Northern blotting using labeled probes that hybridize to transcripts encoding all or part of DJ-1 gene; amplification of mRNA expressed from DJ-1 gene using gene-specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization; and detection of a reporter gene. The term "quantifying" or "quantitating" when used in the context of quantifying transcription levels of DJ-1 gene can refer to absolute or to relative quantification. Absolute quantification may be accomplished by inclusion of known concentration(s) of one or more target nucleic acids and referencing the hybridization intensity of unknowns with the known target nucleic acids (e.g. through generation of a standard curve). Alternatively, relative quantification can be accomplished by comparison of hybridization signals to quantify the changes in hybridization intensity and, by implication, transcription level.

Methods to measure protein expression levels of DJ-1 gene include, but are not limited to, Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, and assays based on a property of DJ-1 including but not limited to ligand binding, or interaction with other protein partners.

Nucleic acid arrays can also be used for detecting the expression of DJ-1 gene. The production and application of arrays in gene expression monitoring have been disclosed previously in, for example, PCT Publication Nos. WO 97/10365, WO 92/10588, WO 95/35505, U.S. Pat. Nos. 6,040,138 and 5,445,934, Hacia et al. (1996) *Nature Genetics* 14:441-447, Lockhart et al. (1996) *Nature Biotechnol.* 14:1675-1680, and De Risi et al. (1996) *Nature Genetics* 14:457-460, all of which are incorporated herein by reference in their entirety. In general, in an array, an oligonucleotide, a cDNA, or genomic DNA, that is a portion of DJ-1 gene, occupies a known location on a substrate. A nucleic acid target sample is hybridized with an array of such oligonucleotides and then the amount of target nucleic acids hybridized to each probe in the array is quantified. One preferred quantifying method is to use confocal microscope and fluorescent labels. The Affymetrix GeneChip™ Array system (Affymetrix, Santa Clara, Calif.) and the Atlas™ Human cDNA Expression Array system are particularly suitable for quantifying the hybridization; however, it will be apparent to those of skill in the art that any similar systems or other effectively equivalent detection methods can also be used. One can use the knowledge of DJ-1 gene to design arrays of polynucleotides, cDNAs or genomic DNAs for screening methods described herein. Such novel pluralities of polynucleotides are contemplated to be a part of the invention.

In general, typical clinical samples that can be used to determine DJ-1 expression include, but are not limited to, blood or blood cells such as white blood cells (e.g., granulocytes and monocytes), spinal fluid, synovial fluid, buccal swabs, tissues, urine, saliva, etc.

The expression level of DJ-1 can also be determined by conjugation or ligand-binding interaction using a DJ-1 ligand and/or DJ-1 antibody that is detectably marked.

Detectable markers suitable for use in the invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and colorimetric labels such as colloidal gold or colored glass or plastic (e.g., polystyrene, polypropylene, latex, etc.) beads.

The present inventors have found that stimulating a subject to over-express DJ-1 improved a clinical condition associated with a neurodegenerative disease. Without being bound by any theory, it is believed that such an improvement is due in some instances at least in part by tolerance to oxidative stress by selectively upregulating the rate limiting step in glutathione synthesis. It was found that when a different metabolic insult was imposed, e.g., A53T mutant α-synuclein, it was found that DJ-1 turned on production of the chaperone protein Hsp-70 without affecting glutathione synthesis.

The present inventors have discovered that histone deacetylase ("HDAC") inhibitors, such as phenylbutyrate, or a derivative thereof, a prodrug thereof, or a salt thereof, increased DJ-1 expression in the N27 dopamine cell line and rescued cells from oxidative stress and mutant α-synuclein toxicity. The terms "pro-drug" and "prodrug" are used interchangeably herein and refer to a pharmacologically substantially inactive derivative of a parent drug molecule that requires biotransformation, either spontaneous or enzymatic, within the organism to release the active drug. Prodrugs are variations or derivatives of the compounds that have groups cleavable under metabolic conditions. Prodrugs become compounds that are pharmaceutically active in vivo when they undergo solvolysis under physiological conditions or undergo enzymatic degradation. Prodrugs may undergo a number of biotransformation steps to release the active drug within the organism. Prodrug forms often offer advantages of solubility, tissue compatibility, or delayed release in the mammalian organism (see, Bundgard, *Design of Prodrugs*, pp. 7-9, 21-24, Elsevier, Amsterdam 1985 and Silverman, *The Organic Chemistry of Drug Design and Drug Action*, pp. 352-401, Academic Press, San Diego, Calif., 1992). Prodrugs commonly known in the art include acid derivatives that are well known to one skilled in the art, such as, but not limited to, esters prepared by reaction of the parent acids with a suitable alcohol such as diglycerol, triglycerol, etc., or amides prepared by reaction of the parent acid compound with an amine, or basic groups reacted to form an acylated base derivative. Prodrugs include compounds wherein an amino acid residue, or a polypeptide chain of two or more (e.g., two, three or four) amino acid residues that are covalently joined through peptide bonds to free amino, hydroxy or carboxylic acid groups of the parent compounds. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, omithine and methionine sulfone. Prodrugs also include compounds wherein carbonates, carbamates, amides and alkyl esters that are covalently bonded to the above substituents of a compound of the invention through the carbonyl carbon prodrug sidechain.

Accordingly, some aspects of the invention provide a method for treating a neurodegenerative disease by administering a histone deacetylase inhibitor, or a derivative thereof, a prodrug thereof, or a salt thereof. Whether a particular compound is an HDAC inhibitor can be readily determined, for example, by an in vitro experimentation. Such experimental procedures are well known to one skilled in the art. Moreover, many HDAC inhibitors are well known. Exemplary HDAC inhibitors include, but are not limited to, TSA, DPAH, Tubastatin A, MGCD, hydroxamic acids (or hydroxamates), such as trichostatin A, vorinostat (SAHA), belinostat, LAQ824, and panobinostat; cyclic tetrapeptides (such as trapoxin B), and the depsipeptides; benzamides such as entinostat, CI994, and mocetinostat; electrophilic ketones; and the aliphatic acid compounds such as phenylbutyrate and valproic acid.

The present inventors have discovered that in mice, phenylbutyrate treatment led to a 260% increase in brain DJ-1 levels and protected dopamine neurons against 1-methyl 4-phenyl 1,2,3,6-tetrahydropyridine (MPTP) toxicity. In a transgenic mouse model of diffuse Lewy body disease, long-term administration of phenylbutyrate reduced α-synuclein aggregation in brain and prevented age-related deterioration in motor and cognitive function. Accordingly, the present inventors have discovered that compounds that upregulate DJ-1 gene expression slow the progression of a neurodegenerative disease, such as Parkinson's disease, by moderating oxidative stress and protein aggregation.

For the sake of clarity and brevity, the present invention will be described with regard to treating Parkinson's disease using a composition comprising a compound that increases DJ-1 expression or the activity of DJ-1 protein. However, it should be appreciated that the method of the invention can be used to treat other neurodegenerative diseases including, but not limited to, Alzheimer's disease, Huntington's disease, Multiple System Atrophy, Progressive Supranuclear Palsy, Down syndrome, diffuse Lewy body disease, and amyotrophic lateral sclerosis.

Dopamine cell death in Parkinson's disease (PD) results from both genetic and environmental factors (1-5). Six genes have been linked to PD including α-synuclein, Parkin, UCHL1, DJ-1, PINK1, and LRRK2 (6-7). α-Synuclein mutations (A53T, A30P, and E46K) cause autosomal dominant forms of PD (8-10). Even in sporadic cases of PD, aggregated α-synuclein has been found to be a major component of Lewy bodies (11-13). The toxicity of mutant forms of α-synuclein results from increased formation of oligomeric and fibrillar aggregates (14-17). The present inventors have demonstrated, as well as others, that expression of A53T mutant α-synuclein results in protein aggregation and cell death in cultured dopamine neurons (18-22).

Mutations in the DJ-1 gene (PARK7) lead to early-onset, autosomal recessive Parkinson disease (23-26). Ordinarily, DJ-1 protects cells by a number of mechanisms. The protein can self-oxidize by forming cysteine-sulfinic acid under oxidizing conditions, thereby shifting its pI from 6.1 to 5.8 (27-28). DJ-1 can sequester the cell death protein Daxx and prevent Daxx-induced apoptosis after oxidative stress (29). DJ-1 can stabilize Nrf2 (nuclear factor erythroid 2-related factor) by preventing association with its inhibitor protein, Keap1, thereby blocking the subsequent ubiquitination of Nrf2 (30).

The present inventors have shown that overexpression of WT DJ-1 can protect dopamine neurons from oxidative stress by increasing cellular glutathione (GSH) levels through selective upregulation of the rate limiting step in GSH synthesis-glutamate cysteine ligase (GCL) (31). The present inventors have also discovered that over-expression of WT DJ-1 inhibits A53T human α-synuclein protein aggregation and reduces neural toxicity in N27 cells by upregulating heat shock protein 70 (Hsp70) without changing glutathione synthesis. Therefore, it is believed that DJ-1 acts through independent, distinct mechanisms to protect cells from different metabolic challenges.

The present inventors have found that over-expression of DJ-1 in the brain provides broad protection from metabolic insults. DJ-1 is important for both the oxidative stress response and the elimination of abnormal protein aggregates. Recently, histone deacetylase inhibitors (HDACi), such as sodium phenylbutyrate (PB) and sodium butyrate (SB), have shown neuroprotective function in several neurodegenerative disease animal models (32-35). The present inventors have discovered that phenylbutyrate and sodium butyrate can increase DJ-1 expression and prevent cell death following oxidative stress. In the MPTP mouse model, the present inventors have found that elevating DJ-1 expression by PB administration reduced the toxicity of MPTP to dopamine neurons. Using the newly established Y39C α-synuclein transgenic mouse model of age-related diffuse Lewy body disease (36), the present inventors have shown that PB can prevent mutant α-synuclein-induced protein aggregation and improve motor and cognitive function.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

The abbreviations used are: ALD, adrenoleukodystrophy-related gene; GSH, glutathione; GCL, glutamate cysteine ligase; GFP, green fluorescent protein; HEK, human embryonic kidney; HRP, horseradish peroxidase; LB, Lewy body; SMN, survival motor neuron; nTg, non-transgenic.

Culture of N27 Cells, HDAC Inhibitor Treatment, and Oxidative Stress Treatment:

Dopaminergic cells derived from embryonic day 12 rat mesencephalon and immortalized with the SV40 large T antigen designated 1RB3AN27, (N27 cells) were used (37). N27 cells were cultured in 6-well or 24-well plates in RPMI 1640 medium containing 10% fetal bovine serum. Cells were treated with sodium phenylbutyrate and sodium butyrate at different concentrations for 48 hr, followed by exposure to varying doses of toxin for 24 hr.

Culture of N27 Cells, A53T α-Synuclein Adenovirus Transduction, shDJ-1 Knockdown of Endogenous DJ-1, and Oxidative Stress Treatment:

N27 cells were cultured in 6-well or 24-well plates in RPMI 1640 medium containing 10% fetal bovine serum and treated with HDAC inhibitor for 48 hr. To transduce cells, A53T α-synuclein adenovirus was mixed with culture medium and incubated with cells for 24 hr at a concentration of 200 plaque forming units (pfu)/cell. To knock down endogenous DJ-1, N27 cells were incubated with adenovirus expressing single hairpin rat DJ-1 (Ad-shDJ-1) at 200 pfu/cell as described previously (31). Two days after adenovirus transduction, cells were exposed to drugs at varying doses for 24 hr: $H_2O_2$ (0-100 μM) and 6-OHDA (0-100 μM).

Immunocytochemistry.

Cultured cells were fixed with 4% paraformaldehyde and processed for immunocytochemistry as described (31,38).

The antibodies included mouse anti-α-synuclein (1:300, Transduction Laboratories); mouse antihuman DJ-1 (1:500, Stressagen); rabbit anti-DJ-1 (1:500, Chemicon); and rabbit anti-TH (tyrosine hydroxylase, 1:200, PelFreez).

MTT Assay and Apoptosis Evaluation.

At the end of each experiment, methylthiazoletetrazolium (MTT) was added to the culture medium (final concentration 0.4 mg/mL) and incubated for two hours. Cell viability was measured by a microplate reader as described (31, 38). The nuclear dye Hoechst 33258 (10 µg/ml) was used to visualize and count apoptotic cells.

Western Blotting.

N27 cells were cultured in 6-well plates and treated with compounds as described above. Cells were lysed in a dissociation buffer containing 50 mM Tris-HCl, 10 mM NaCl, 0.1% Triton X-100 plus protease inhibitor cocktail (Roche). The mouse brain tissues were dissected and quickly frozen in dry ice. Tissues were thawed on ice and homogenized in dissociation buffer with protease inhibitors (Roche). Protein concentration was determined by the BCA method (Pierce). Fifty µg of protein was separated on 10% SDSPAGE gel and transferred to a nitrocellulose membrane. After blocking nonspecific binding, membranes were incubated with antibodies to DJ-1 (1:5000, Chemicon), α-synuclein (1:3000, Transduction Laboratories), TH (1;2000, PelFreez), and β-actin (1:4000, Sigma). Blots were incubated with HRP-conjugated secondary antibody (1:10,000; Jackson Immuno Research), followed by chemiluminescent detection (Perkin Elmer Life Sciences) (31, 38).

Luciferase Assay.

The luciferase assay was based on the pGLuc-Basic vector (NEB). The human DJ-1 2 kb promoter area was amplified by PCR using genomic DNA from HEK293 cells. The human DJ-1 promoter was then cloned into the pGLuc-Basic vector, and that reporter vector was transfected into HEK293 cells. G418 (200 µg/ml) was applied to the cultures, and resistant clones were selected and assayed for luciferase activity. Stable cell lines expressing pDJ1-Luciferase were treated with PB and SB for 48 hr at various concentrations in 24-well plates. Culture medium samples (20 µl) were incubated with *Gaussia* luciferase assay substrate (NEB), and luminescence was measured in a 96-well plate reader (BioTek Synergy HT Multi-Mode microplate reader).

Phenylbutyrate and Butyrate Treatment in Mice.

Adult C57BL/6 mice (4-6 months old) were treated with PB and SB in drinking water for 14 days. The PB and SB were dissolved in water at concentrations of 500, 1000, 1500, and 2000 mg/L. Mice typically drink 4-5 ml of water per day, and their drinking volumes were not affected by the addition of PB or SB. Control animals received water with sodium chloride added to the same molarity as the sodium in the drug-treated animals. Brain tissues were dissected and immediately frozen in dry ice for Western blot analysis using DJ-1, α-synuclein and β-actin antibodies.

MPTP Injection into Mice.

Adult C57BL/6 mice (4-6 months old) were treated with PB in drinking water (1000 mg/L, 5.4 mM) for two weeks, followed by injection of 1-methyl 4-phenyl 1,2,3,6-tetrahydropyridine (MPTP-HCl, dissolved in sterile saline, Sigma-Aldrich) four times at 2-hr intervals (20 mg/kg, i.p.). Treatment with PB continued after MPTP injection. Control animals received identical injections of MPTP, but had only sodium chloride added to drinking water as described above. One week after MPTP lesioning, mouse brain tissues were dissected for Western blot and HPLC analysis.

HPLC Analysis of Dopamine and DOPAC.

Mouse striatum was frozen in dry ice, sonicated in ice-cold 0.2 m perchloric acid and centrifuged at 15,000 g for 15 min at 4° C. An aliquot (5 µL) of the supernatant solution was analyzed by HPLC equipped with an electrochemical detector (CoulArray system ESA Model 5600; ESA, Boston, Mass., USA), a pump (ESA Model 580) set at 1.5 mL/min, and a reverse-phase C18 column (3 µm, 100 Å~4.6 mm, Waters, Milford, Mass., USA). The mobile phase was composed of 100 mm citric acid, 2% methanol, 1 mm EDTA and 5 mg/L sodium octyl sulfate (pH 3.0).

Transgenic Mice Expressing Human Y39C α-Synuclein Under Mouse Thy-1 Promoter.

Y39C human α-synuclein transgenic mouse model has been described by the present inventors (36). Briefly, human Y39C α-synuclein cDNA was cloned into the mouse pThy-1 vector at the NotI site. The construct was microinjected into mouse oocytes, and founder mice were identified by PCR and Southern blotting analysis. Mice were bred to establish stable transgenic lines. Expression of human Y39C α-synuclein in these transgenic mice was determined by immunostaining and Western blotting with antibodies specific to human α-synuclein (LB509).

Drug Treatment in !-Synuclein Transgenic Mice.

The Y39C α-synuclein transgenic mice were divided into younger (6-8 months=Young Tg) and older (10-12 months=Old Tg) groups. Each group received PB (1000 mg/L, 5.4 mM) or vehicle (NaCl) in the drinking water for 3 months. Animals were tested for rotarod and water maze performance after 6-weeks and 12-weeks of treatment.

Rotarod Test.

Mice were tested for their ability to run on a 3 cm diameter rotating rod (rotarod) at speeds ranging from 3 to 33 rpm. The protocol consisted of two phases: habituation (Day 1) and rotarod training/testing (Days 2 to 5). During habituation on Day 1, the mice were trained to remain on the rotarod at 3 rpm. During training/testing on Days 2 to 5, mice were placed on the rotating rod at a constant speed for three one-minute trials with a 5 minute rest interval between trials. Each test day, the speed was increased, reaching 33 rpm by Day 5. The time the mice spent on the rotarod without falling was recorded for each trial.

Morris Water Maze Testing.

Spatial learning was assessed using the Morris water maze. The maze included a circular tank (120 cm in diameter) filled to 10 cm below the edge of the tank with 27° C. water that was made opaque by the addition of non-toxic black ink. A circular escape platform (10 cm in diameter) was located 1 cm below the surface of the water in a constant location in the northwest quadrant of the tank. Mice were first acclimated to the maze during three trial habituation sessions. Each testing session consisted of three consecutive days with four trials per day. The platform was invisible in the pool, and mice were allowed to swim for 60 sec before being returned to the home cage. The latency from all training and testing sessions was collected.

Immunohistochemistry and α-Synuclein Staining.

The mice were sacrificed by deep anesthesia followed by intracardiac perfusion with saline and 4% paraformaldehyde. The mouse brains were cryosectioned at 40 µm. Immunohistochemistry was performed using antibodies to human α-synuclein (LB509, 1:500). Immunostaining was developed with diaminobenzidine (DAB). Tissue sections were examined for the Lewy body-like inclusions.

Statistics.

All experiments were repeated at least three times. Data were analyzed using multivariate ANOVA and the Fisher LSD post hoc test. Significance was set at p<0.05. Values are shown as mean±SEM.

RESULTS

Sodium Phenylbutyrate (PB) and Sodium Butyrate (SB) Increase DJ-1 Expression in N27 Cells and HEK293 Cells.

Using the N27 rat dopaminergic cell line, a number of compounds were screened for their ability to increase DJ-1 expression. From this screen, it was found that sodium phenylbutyrate and sodium butyrate increased DJ-1 protein levels to 300% of control after two days treatment as shown in FIG. 1A. Both compounds had peak effects at concentrations of 0.15-0.3 mM (**p<0.01 compared to control, FIG. 1B-C). To test if PB and SB directly upregulated DJ-1 gene transcription, an HEK293 reporter cell line was created which stably expressed the human DJ-1 promoter-luciferase construct. The HEK293 reporter cells were treated with PB and SB for 48 hr, followed by luciferase assay. It was found that both PB and SB increased luciferase activity as well as DJ-1 protein levels (*p<0.05, **p<0.01 compared to control, FIG. 1D-E). These results indicate that enhanced DJ-1 gene transcription is responsible for the higher DJ-1 protein levels seen after PB and SB treatments.

Sodium Phenylbutyrate Protects N27 Cells from Oxidative Stress and α-Synuclein Induced Toxicity.

Figure 2:
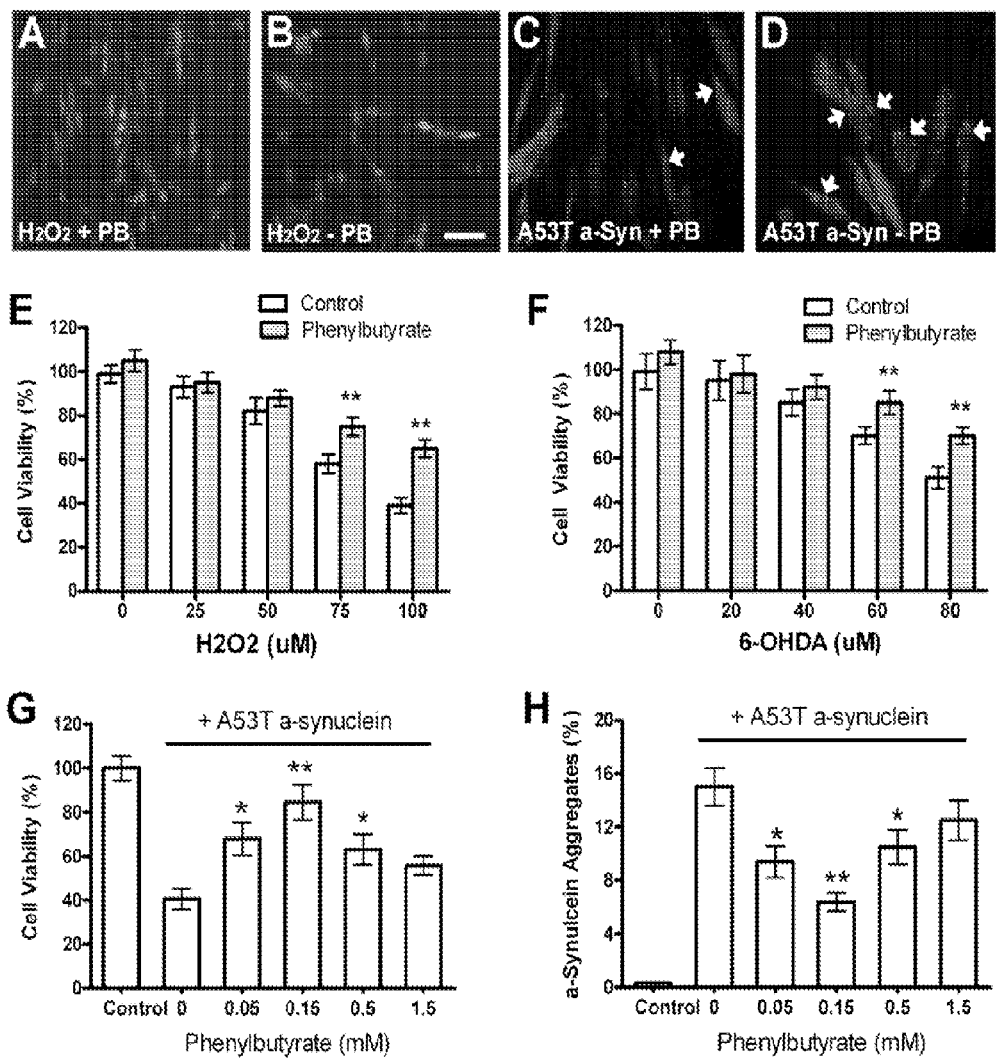
FIGS. 2A-B are sample images of GFP adenovirus expression showing protective effects of sodium phenylbutyrate in N27 cells that were incubated with PB for 48 hr, followed by 24 hr treatment with $H_2O_2$ or 6-OHDA at various concentrations
FIGS. 2C and 2D are sample images of α-synuclein antibody LB509 staining showing protective effects of sodium phenylbutyrate in N27 cells that were incubated with PB for 48 hr, followed by 48 hr treatment of adenovirus expressing A53T human α-synuclein (200 pfu/cell).
FIGS. 2E-2H are bar graphs of quantitative data from sample images of 2A-2D, respectively. Three random fields (150-200 cells per field) were examined to determine the percentage of cells with α-synuclein aggregates (arrows in G-H). Triplicate treatments in 24-well plates were used and experiments were repeated three times. ($*p<0.05$, $**p<0.01$ compared to control, n=9). Cell viability was determined by MTT assays.

The present inventors have previously shown that overexpression of the DJ-1 gene through adenoviral transduction can make N27 cells more resistant to oxidative stress and mutant α-synuclein toxicity (31). To see if phenylbutyrate could replicate these protective effects, N27 cells were treated with 0.15 mM sodium phenylbutyrate for two days and then subjected cells to oxidative stress for 24 hr. FIGS. 2A and B show sample images of N27 cells with or without PB followed by $H_2O_2$ treatment, in which cells were identified by GFP adenovirus expression. Quantitative results showed that PB treatment significantly increased cell viability after exposure to hydrogen peroxide ($H_2O_2$) and 6-hydroxydopamine (6-OHDA) compared to controls (*p<0.05, **p<0.01, FIGS. 2 E,F).

The present inventors have earlier demonstrated that expression of A53T mutant human α-synuclein in N27 cells led to cell death with α-synuclein-positive cytoplasmic aggregates (31, 38). In the present experiments, N27 cells were treated with PB for two days. Cells were then exposed to adenovirus expressing A53T mutant α-synuclein for another two days. FIGS. 2C and D show sample images of N27 cells with or without PB treatment followed by A53T α-synuclein expression, in which cells were identified by α-synuclein immunostaining. It was found that PB treatment increased cell viability and reduced the number of cells with α-synuclein aggregates (*p<0.05, **p<0.01 compared to control, FIG. 2G-H). These data indicate that phenylbutyrate can protect dopamine cells from oxidative stress and mutant α-synuclein toxicity.

Knocking Down DJ-1 Blocks Phenylbutyrate Effects in N27 Cells.

Figure 3:
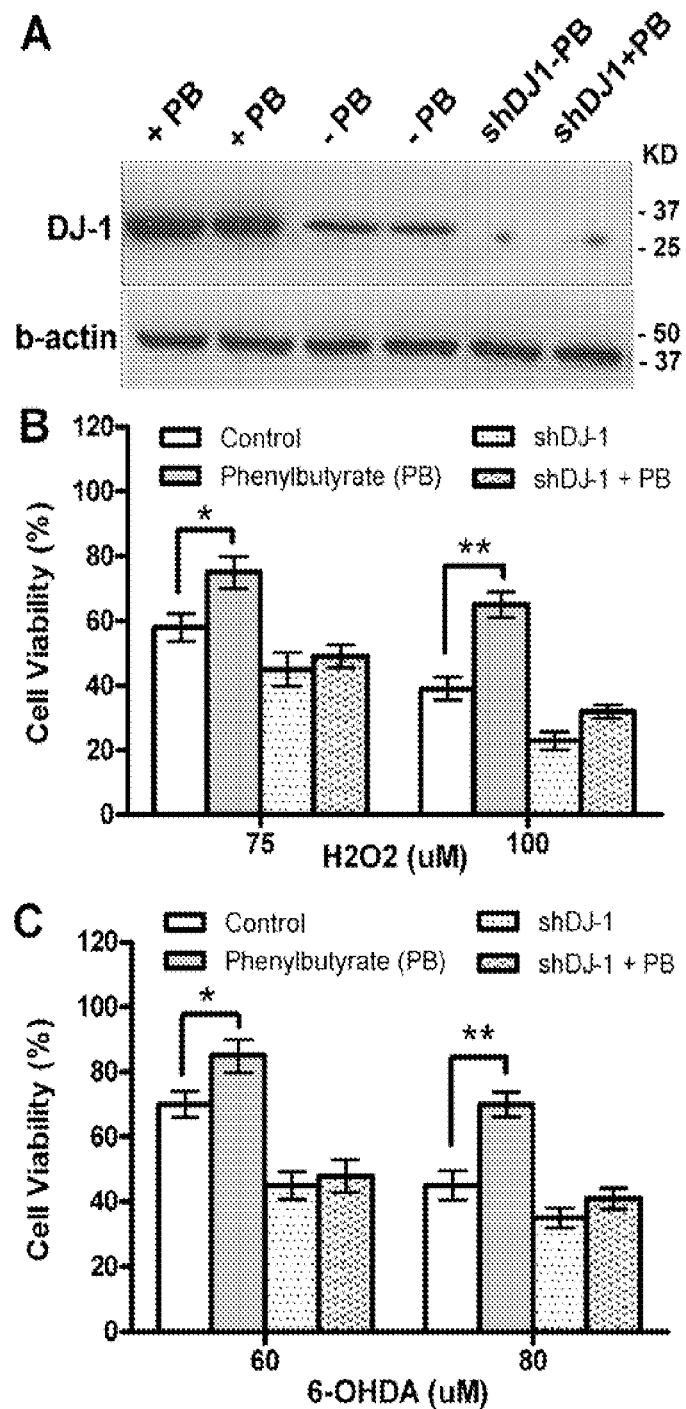
FIG. 3A is a Western blot showing that knockdown of endogenous DJ-1 abolishes neuroprotection from sodium phenylbutyrate.
FIGS. 3B and 3C are bar graphs showing cell viability data as measured by MTT assay. ($*p<0.05$, $**p<0.01$ compared to control, n=9).

To test whether DJ-1 is needed for the protective actions of PB, the present inventors have used knock-down technology. With an adenovirus expressing shDJ-1 (31), DJ-1 gene expression was knocked down in N27 cells (FIG. 3A) and then tested whether PB could rescue cell death resulting from $H_2O_2$ (75 μM or 100 μM) and 6-OHDA (60 μM or 80 μM). Results showed that DJ-1 knockdown in N27 cells effectively abolished the neuroprotective effect of PB against $H_2O_2$ and 6-OHDA-induced toxicity (compare columns with horizontal and vertical bars to control in FIGS. 3B-C), while naïve N27 cells with PB treatment significantly improved cell viability (*p<0.05, **p<0.01 compared to control, FIGS. 3B, C).

These in vitro experiments demonstrate that phenylbutyrate can turn on expression of the DJ-1 gene and protect N27 cells from oxidative stress and mutant α-synuclein toxicity. Importantly, activation of DJ-1 is required for the phenylbutyrate effect.

Sodium Phenylbutyrate and Sodium Butyrate Increase DJ-1 Expression in Mice.

With the finding that PB and SB provide a way to turn on DJ-1 gene expression in vivo and thereby protect brain from neurotoxic stress, mice were treated with these drugs. Because phenylbutyrate is stable in solution and has a very short half-life (50 min) in vivo, drugs were delivered in drinking water. Adult C57BL/6 mice were treated with PB or SB at various concentrations in drinking water for two weeks. Control mice received water with equimolar concentrations of sodium chloride. It was found that all treatment and control groups consumed similar volumes of water, and the intake for all was in the range expected for normal daily fluid consumption (data not shown). Animals were sacrificed by an overdose of anesthetic, and brains removed and frozen on dry ice. Brain tissues were analyzed for DJ-1 protein levels by Western blotting. Results showed PB and SB significantly increased DJ-1 levels (*p<0.05, **p<0.01 compared to control, FIG. 4A-C).

Figure 4:
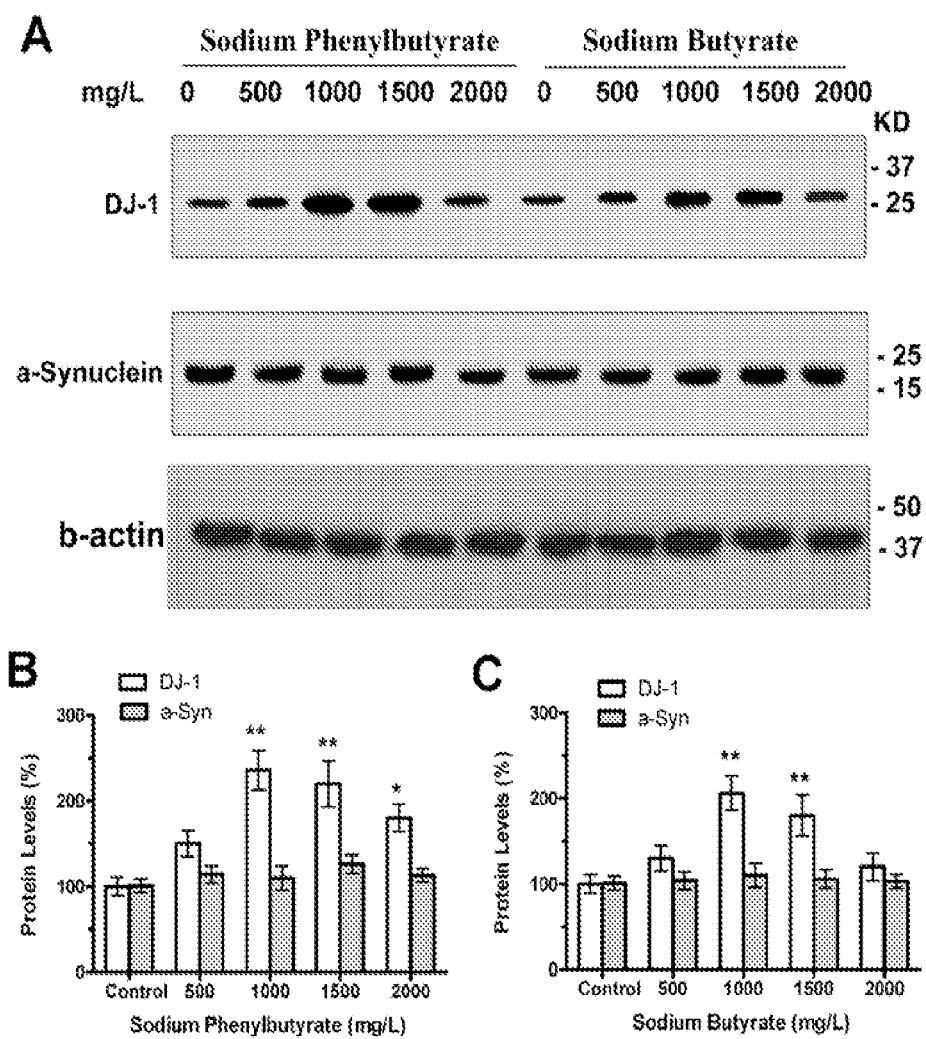
FIG. 4A is a Western blot of mouse brain tissues with DJ-1, α-synuclein and 1-actin antibodies showing sodium phenylbutyrate and sodium butyrate increased DJ-1 expression.
FIGS. 4B and 4C are quantitative data of DJ-1 and α-synuclein levels after PB and SB treatment ($*p<0.05$, $**p<0.01$ compared to control, n=4).

To test whether the increase in DJ-1 was caused by a global increase in gene and protein expression, endogenous α-synuclein protein levels were also measured as shown in FIG. 4A-C. α-Synuclein concentrations were not changed after drug treatment, suggesting that PB and SB showed selectivity in producing an increase in DJ-1 expression in brain. To study the time course of DJ-1 expression during chronic drug administration, DJ-1 levels were examined in mice treated with PB in the drinking water for 1, 2, and 3 months. It was found that brain DJ-1 reached plateau values after two weeks of PB, and those levels were sustained for 1 to 3 months of treatment (data not shown). These data indicate that PB can provide sustained elevation of DJ-1 expression in mouse brain.

Sodium Phenylbutyrate Protects Dopamine Neurons from MPTP-Induced Neurotoxicity.

Figure 5:
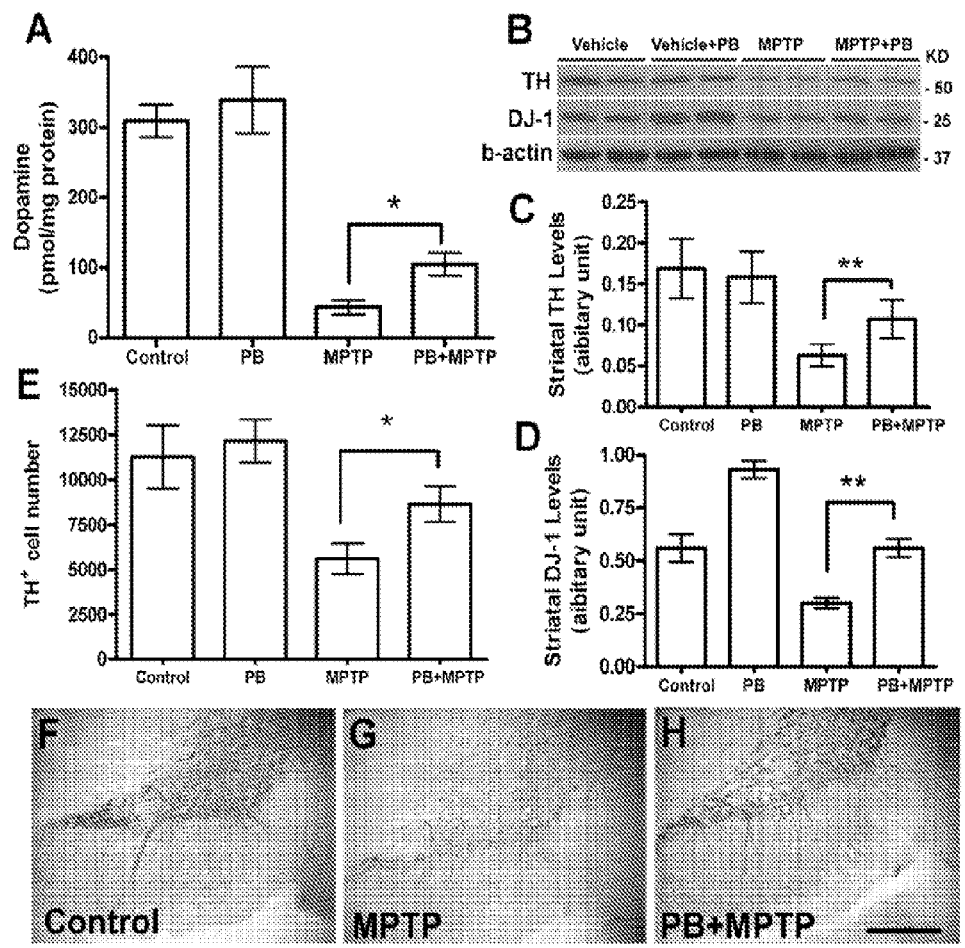
FIGS. 5A-5H are bar graphs (5A, 5C, 5D and 5E), Western blots (5B), and images showing sodium phenylbutyrate prevented mouse dopamine neuron death after MPTP lesion (Bar length, 1 mm for F-H).

To evaluate whether pre-treatment with PB can protect dopamine neurons in the MPTP mouse model of Parkinson's disease, adult C57BL/6 mice were treated with PB in the drinking water (1000 mg/L) for two weeks. They were then injected with MPTP 4 times at 2 hr intervals (20 mg/kg, i.p., each injection). One week after MPTP injections, mice were sacrificed for biochemical and histological analysis. It was found that PB-pretreatment significantly increased striatal dopamine levels as measured by HPLC (*p<0.05 compared to MPTP alone, FIG. 5A). PB treatment also increased tyrosine hydroxylase (TH) protein levels in striatum (Western blot, p<0.01 compared to MPTP alone, FIG. 5B-C). Furthermore, DJ-1 levels in striatum were significantly increased in PB-treated mice (Western blot, p<0.01 compared to MPTP alone, FIG. 5B, D). It was also found that PB treated mice had significantly higher numbers of TH positive dopamine neurons in the substantia nigra (*p<0.05 compared to MPTP alone, FIG. 5E). Sample immunohistochemical images showing increased survival of TH-positive dopamine neurons in substantia nigra are presented in FIG.

5F-H. These data indicate that phenylbutyrate can protect dopamine neurons from MPTP neurotoxicity.

Sodium Phenylbutyrate Prevents Age-Related Motor and Cognitive Decline in Mice with Diffuse Lewy Body Disease.

The present inventors have created a transgenic mouse model expressing a tyrosine-to-cysteine (Y39C) mutant human α-synuclein (36). Because the transgene is expressed under control of the Thy1 promoter, mutant protein accumulates throughout the brain in all neurons. These animals have progressive, age-related decline in motor and cognitive function. Histopathology shows Lewy body-like α-synuclein inclusions in neurons. The age-related behavioral and neuropathologic phenotypes have similarities to PD and diffuse Lewy body disease.

Figure 6:
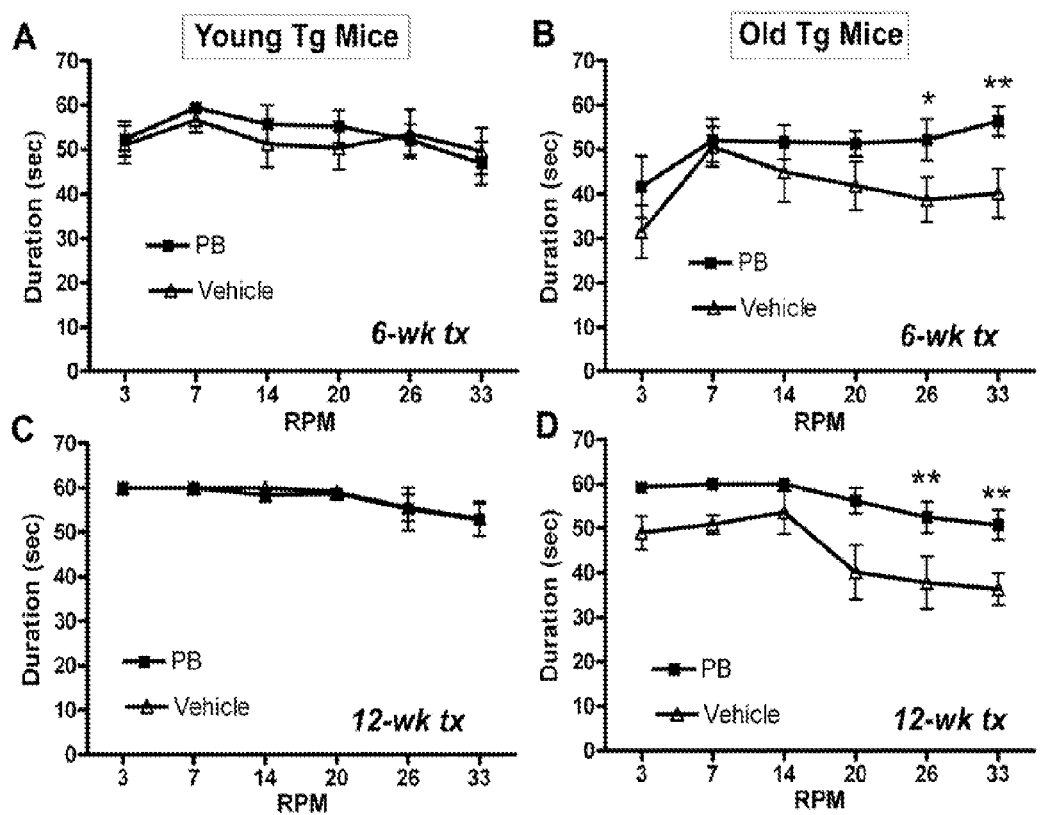
FIGS. 6A-6D are graphs showing sodium phenylbutyrate improved motor function in aged α-synuclein transgenic mice ($*p<0.05$, $**p<0.01$, n=10).

To test whether PB treatment can prevent the development of behavioral and neuropathological deficits in this transgenic mouse model, transgenic mice were divided into a Young Tg group (age 6-8 months) and an Old Tg group (age 10-12 months). Mice were treated with PB (1000 mg/L, 5.4 mM) or vehicle (NaCl, 310 mg/L) in drinking water for three months. Mice were tested for motor function after 6 weeks and 12 weeks of treatment using a rotarod with increasing speed (3-33 RPM). Results showed that PB treatment did not change motor function in Young Tg mice at 6-weeks or 12-weeks of therapy when animals were up to 11 months of age (FIG. 6A, C). By contrast, in Old Tg mice, motor function deteriorated progressively with age in animals that were 13 to 15 months old at the end of the study. PB treatment prevented the decline and significantly improved motor function in Old Tg mice at both 6-week and 12-week tests ($*p<0.05$, $**p<0.01$ compared to vehicle, FIG. 6B, D). The Old Tg mice treated with PB performed similarly to Young Tg mice (compare FIGS. 6C and 6D).

Figure 7:
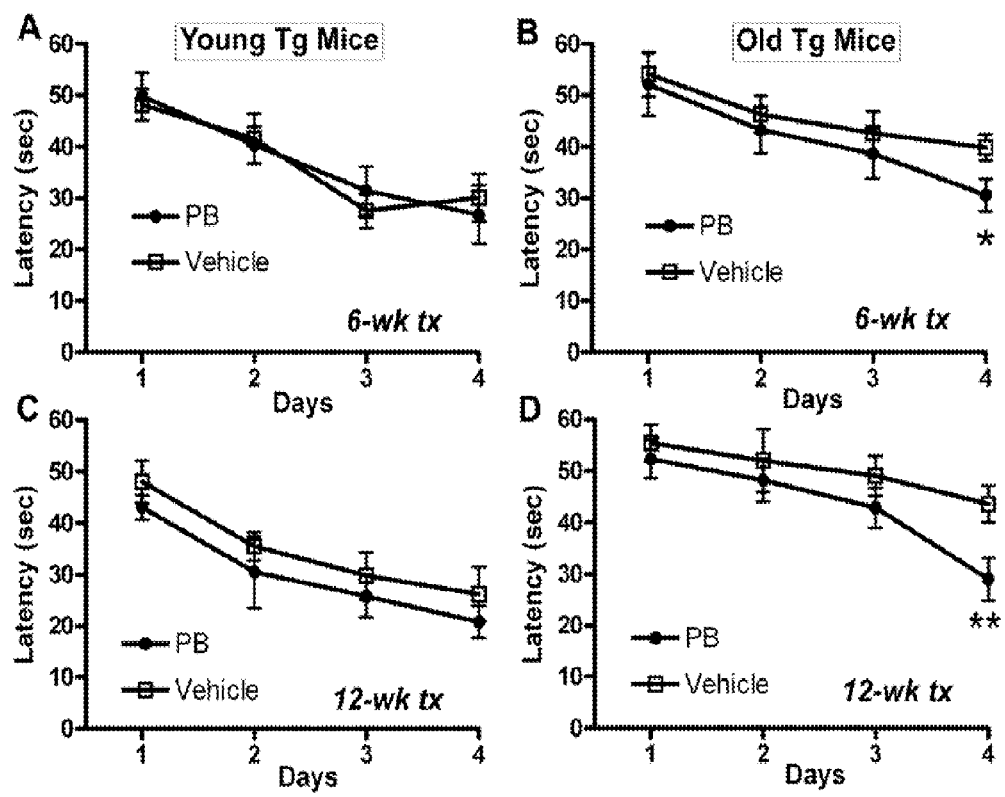
FIGS. 7A-7D are graphs showing sodium phenylbutyrate improved cognitive function in aged α-synuclein transgenic mice ($*p<0.05$, $**p<0.01$, n=10).

Mice were tested for cognitive function at 6 weeks and 12 weeks of treatments using a Morris water maze. In these transgenic mice, the present inventors have reported that water maze performance deteriorates as mice age (36). In the current studies, it was found that Young Tg mice performed well in the Morris water maze, and PB treatment did not change water maze performance at 6-week and 12-week tests (FIG. 7A, C). In Old Tg mice, PB treatment prevented the age-related decline in water maze function at both 6-week and 12-week tests ($*p<0.05$, $**p<0.01$ compared to vehicle, FIG. 7B, D). These results show that sodium phenylbutyrate can improve motor and cognitive function in aged transgenic mice.

Figure 8:
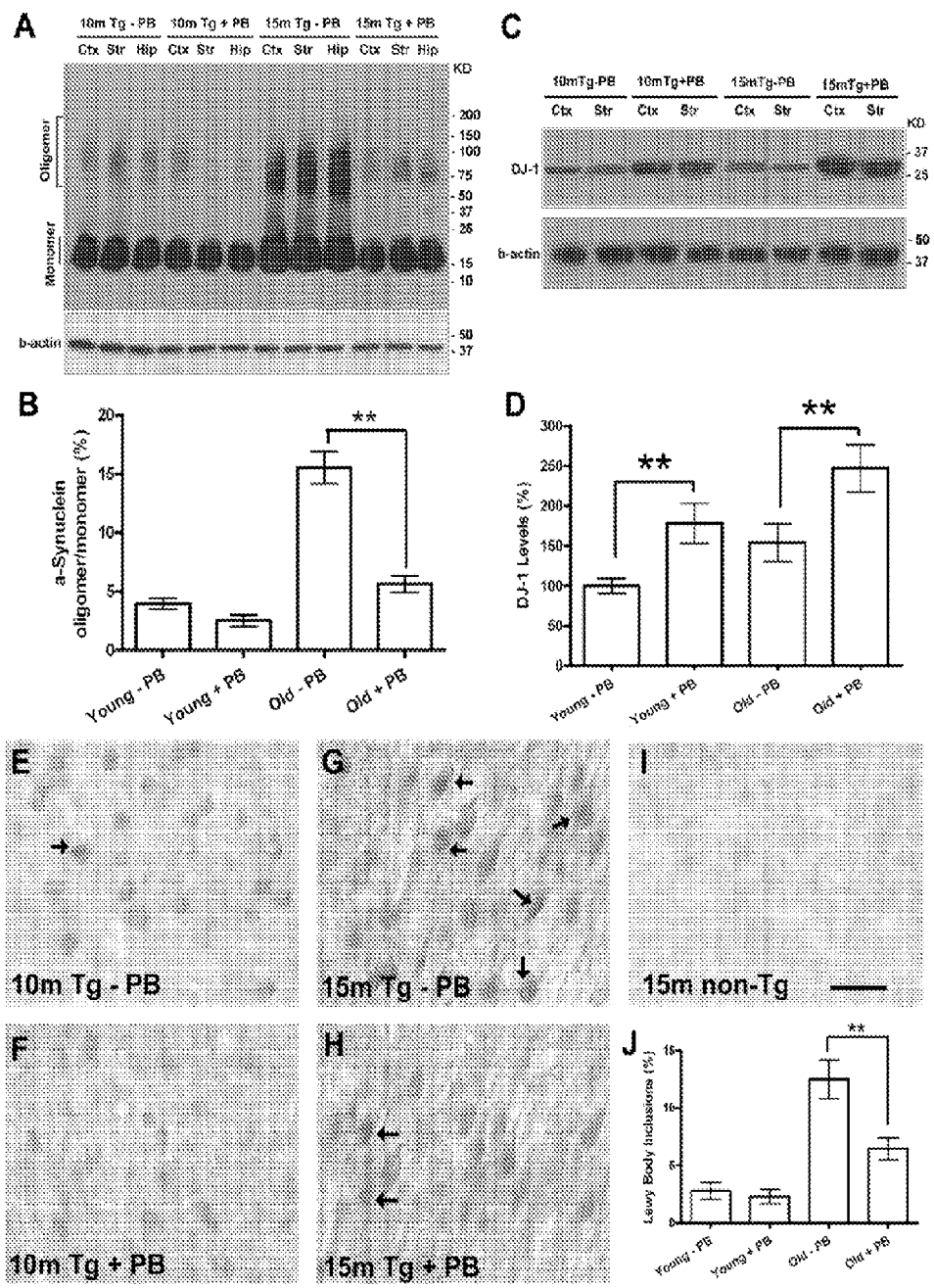
FIGS. 8A-J are Western blots (8A and 8C), graphs of quantitative data results (8B and 8D), brain section images of Young and Old transgenic mice with or without PB treatment that were immunostained with human α-synuclein antibody (LB509) (8E-8I), and a bar graph result showing that sodium phenylbutyrate increased DJ-1 expression and reduced α-synuclein oligomer formation and aggregation in transgenic mice.

Sodium Phenylbutyrate Reduces α-Synuclein Aggregation and Increases Expression of DJ-1 in Old Transgenic Mouse Brain.

α-Synuclein aggregation was examined in transgenic mice treated with PB. Brain tissue lysates were separated in SDS-PAGE and probed with α-synuclein antibody. FIG. 8A shows Western blot images from young and old mice. Brain from a 15-month old transgenic mouse (15m Tg–PB) showed intense α-synuclein oligomer fractions in cortex, striatum and hippocampus. PB treatment dramatically reduced oligomer formation in an age-matched transgenic mouse (15m Tg+PB) (FIG. 8A). In 10-month old Young transgenic animals, oligomer accumulation had not yet occurred, and the effect of PB was minimal (10m Tg–PB and +PB) (FIG. 8A). FIG. 8B presents the ratios of α-synuclein oligomer to monomer. The very high level of oligomer in old transgenic mice (Old w/o PB) is dramatically reduced by treatment ($**p<0.01$, FIG. 8B). In these same treatment groups, it was found that brain DJ-1 protein levels were significantly increased in both young and old transgenic mice treated with PB compared to age-matched mice without PB treatment ($*p<0.05$, FIG. 8C-D).

α-Synuclein immunostaining was performed in mouse brain sections using LB509 antibody. The PB treatment had little effect on the number of neurons with Lewy body-like inclusions in young mice (sample images from 10m Tg mice with and without PB are shown in FIG. 8E, F). However, in old mice, the PB treatment greatly reduced the number of neurons with Lewy body-like inclusions (sample images from 10m Tg mice with and without PB are shown in FIG. 8G, H). Control staining from 15 month old non-Tg mice is shown in FIG. 8I. The percentage of α-synuclein positive neurons with Lewy body-like inclusions is shown in FIG. 8J ($**p<0.01$, PB compared to Vehicle). These data indicate that phenylbutyrate can increase DJ-1 expression, reduce α-synuclein oligomer formation, and prevent age-related decline in motor and cognitive function in a transgenic mouse model of diffuse Lewy body disease.

Glycerol Phenylbutyrate.

Glycerol phenylbutyrate (i.e., phenylbutyrate triglyceride) exhibited motor performance improvement in transgenic mice overexpressing human α-synuclein in brain neurons. Glycerol phenylbutyrate is a liquid pro-drug manufactured by Hyperion Pharmaceuticals and is also named H-100. The drug is shown to be metabolized in the gut to produce the active compound phenylbutyrate.

Figure 9:
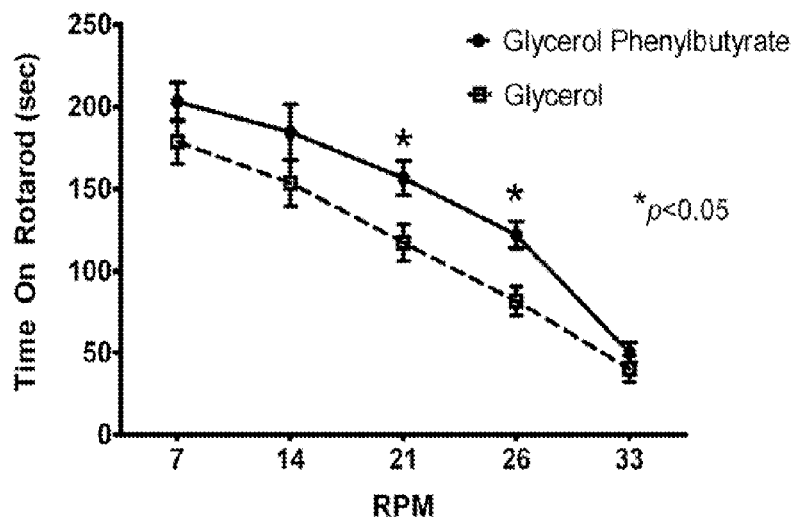
FIG. 9 is a graph showing transgenic animals treated with daily glycerol phenylbutyrate were able to stay on a rotating rod longer than animals receiving only glycerol.

Transgenic mice were genetically programmed from birth to develop a "Parkinson-Plus" condition by depositing an abnormal form of a protein called Y39C-α-synuclein in neurons of the brain under control of the Thy1 promoter (see Zhou et al., *J. Biol. Chem.*, 2008, 283, 9863-70). At one year of age, 8 mice were treated with daily glycerol phenylbutyrate (solid line) and another 8 mice were treated with the inactive compound glycerol (dashed line). After 6 weeks of daily treatment, animals were placed on a rotating rod (Rotarod) at different speeds for up to 5 minutes. Animals which could not keep up with the turning rod fell off. The time they were able to stay on the rod was noted. As shown in FIG. 9, transgenic animals treated with daily glycerol phenylbutyrate were able to stay on the rod longer than animals receiving only glycerol. These differences were statistically significant at the higher speeds, 21 and 26 rpm. At the highest speed, 33 rpm, all animals fell off the rod after about 50 seconds. The improved motor performance is similar to that observed in an earlier study of the same strain of transgenic mice receiving sodium phenylbutyrate in their drinking water (Zhou et al., *J. Biol Chem.*, 2011, 286: 14941-51).

Phenylbutyrate Works by Turning on the Protective Gene DJ-1 in Brain Cells.

DJ-1 makes cells resistant to oxidative stress and resistant to accumulation of abnormal proteins by promoting production of exosomes.

Figure 10:
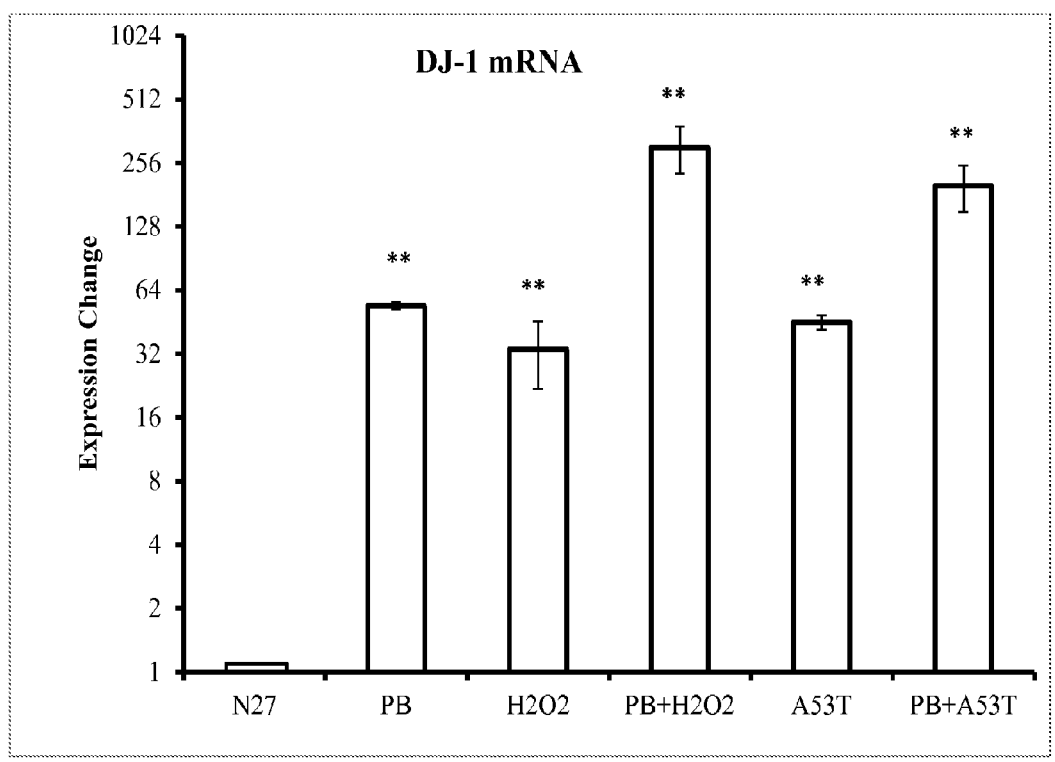
FIG. 10 is a bar graph showing PB increases DJ-1 mRNA in N27 dopamine neurons.

Phenylbutyrate upregulates the protective gene DJ-1 with a 50-fold increase in mRNA in N27 dopamine neurons in tissue culture. Exposure of cells to hydrogen peroxide also increases DJ-1 mRNA. As shown in FIG. 10, in cells pretreated with phenylbutyrate for 48 hours, the combination of phenylbutyrate and $H_2O_2$ led to a greater increase in DJ-1 mRNA (256-fold). Cell stress created by the overexpression of A53T mutant human alpha-synuclein (A53T) increased DJ-1 gene expression, while the combination of phenylbutyrate and A53T caused an even greater increase. Not shown is the fact that cells treated with phenylbutyrate have substantially better cell survival than those exposed to $H_2O_2$ and A53T without phenylbutyrate. When DJ-1 gene expression was blocked by anti-sense RNA, the protective effects of phenylbutyate were eliminated (Zhou et al., *J. Biol Chem.*, 2011, 286: 14941-51).

Figure 11:
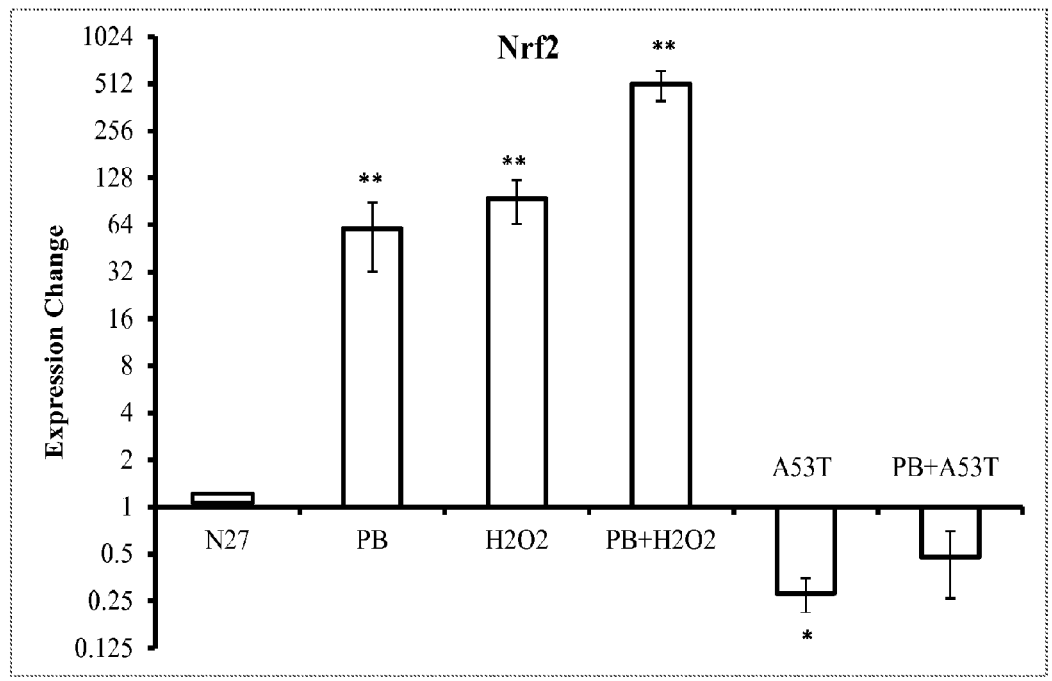
FIG. 11 is a bar graph showing that the oxidative stress pathway Nrf2 is upregulated by phenylbutyrate.

As shown in FIG. 11, the oxidative stress pathway Nrf2 was upregulated by phenylbutyrate with a 50-fold increase in mRNA. Interestingly, overexpression of the mutant protein A53T did not turn on the Nrf2 gene.

Figure 12:
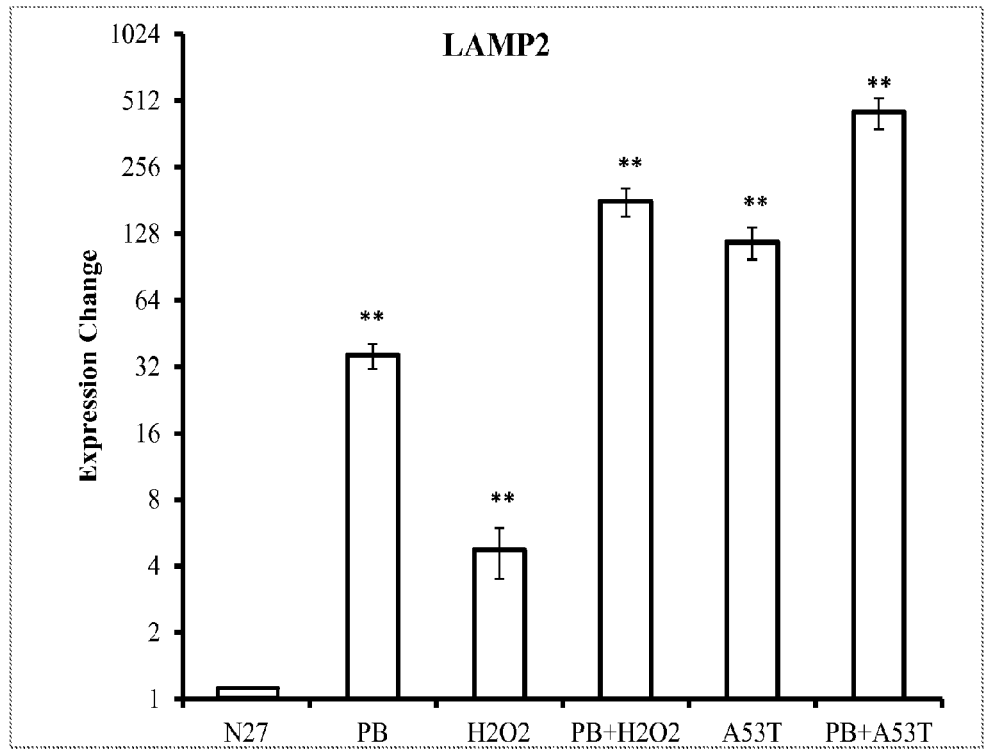
FIG. 12 is a bar graph showing that the lysosomal pathway Lamp2 is activated by phenylbutyrate in N27 dopamine neurons.

In addition, the lysosomal pathway Lamp2 was activated by phenylbutyrate in N27 dopamine neurons. See FIG. 12. The drug increased expression by about 30-fold while $H_2O_2$ led only to a 4-fold increase. Pretreatment with phenylbutyrate for 48 hr followed by $H_2O_2$ increased expression by 200-fold. Similarly, A53T increased expression of Lamp2 as part of the cells' response to abnormal protein stress. Phenylbutyrate amplified that response to a 400-fold increase in gene expression.

Figure 13:
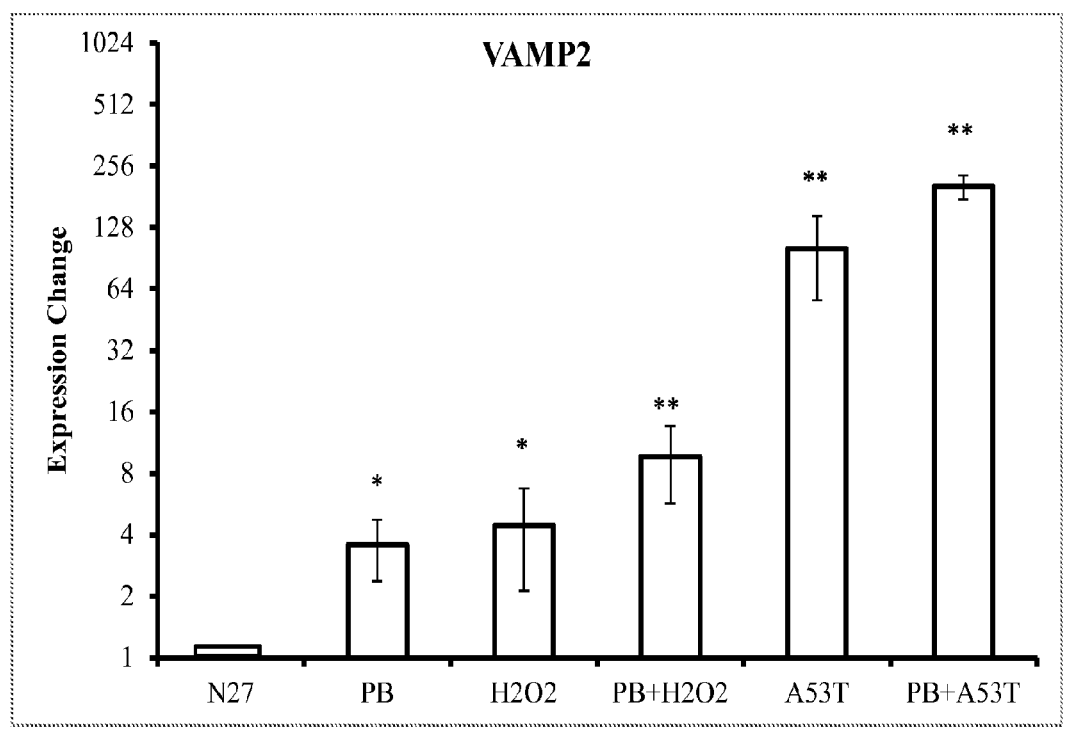
FIG. 13 is a bar graph showing that the vesicle-exosome protein Vamp2 in N27 dopamine neurons is upregulated by mutant protein expression with the addition of phenylbutyrate.

FIG. 13 shows the bar graph of tissue culture results in N27 dopamine neurons showing that the vesicle-exosome protein Vamp2 was upregulated particularly by mutant protein expression with the addition of phenylbutyrate. As can be seen, the exosome marker Vamp2 was upregulated particularly by overexpression of mutant protein A53T human α-synuclein (80-fold). The addition of phenylbutryrate increased that overexpression to 200-fold.

DISCUSSION

The present disclosure describes the neuroprotective effects of HDAC inhibitors (e.g., phenylbutyrate) in both cell culture and in mouse models. It was found that phenylbutyrate can upregulate DJ-1 mRNA and protein levels in rat dopaminergic N27 cells and HEK293 cells. Increased expression of DJ-1 renders cells more resistant to oxidative stress and α-synuclein-induced toxicity. Blocking DJ-1 activation with anti-sense-DJ-1 interferes with the physiologic protection. In mice, the present inventors have discovered that phenylbutyrate given through drinking water can increase brain DJ-1 levels. Upregulation of DJ-1 resulted in neuroprotection for dopamine neurons against MPTP toxicity. Moreover, phenylbutyrate given to transgenic mice that overexpress a mutant form of α-synuclein prevented oligomer formation in brain and stopped the age-related decline in motor and cognitive function.

Phenylbutyrate is a histone deacetylase inhibitor (HDACi) and has been shown to be neuroprotective in animal models of Huntington's disease, spinal muscular atrophy, and amyotrophic lateral sclerosis (33-34, 39-43). The drug has been shown to protect dopamine neurons from death in the MPTP mouse model of Parkinson's disease (35). Phenylbutyrate can protect dopamine neurons from rotenone-induced cell death. In transgenic mice expressing both A53T and A30P human α-synuclein, treatment with phenylbutyrate can improve behavioral function and reduce neuropathology (44-45). These prior studies did not propose a link between phenylbutyrate and the activation of DJ-1 gene expression.

As a histone deacetylase inhibitor, phenylbutyrate can increase acetylation levels of histone H3 and H4, thereby promoting transcriptional activation (33, 46). Previous studies have demonstrated that phenylbutyrate can increase expression of many genes including antiapoptotic genes, components of ubiquitinproteosomal pathways, nuclear factor NF-kB p50, survival motor neuron 1 (SMN1), and adrenoleukodystrophy-related gene (ALD) (40-41, 46-47). Other reports have shown that histone deacetylase inhibitors can activate INK4d and DR5 genes through the Sp1 binding site in the promoters (48-50). Because the DJ-1 gene promoter contains Sp1 binding sequences (51), it is possible that phenylbutyrate increases DJ-1 gene expression by increased binding of Sp1 to the DJ-1 promoter. Our DJ-1 promoter-luciferase reporter assay in HEK 293 cells has provided additional evidence that phenylbutyrate can increase DJ-1 gene expression. The present inventors have found that blocking DJ-1 expression with shDJ-1 blocks the neuroprotective effects of phenylbutyrate.

Increased DJ-1 levels protect against oxidative stress and other biochemical toxicity through multiple pathways. DJ-1 can stabilize Nrf2, a master regulator of antioxidant transcriptional responses, by blocking association with its inhibitor protein Keap1, thereby preventing ubiquitination of Nrf2 (30). DJ-1 can also sequester the cell death protein Daxx in the nucleus and prevent Daxx-induced apoptosis after oxidative stress (29). Recent reports show that DJ-1 can work in parallel with the PINK1/parkin pathway to maintain mitochondrial function in the presence of an oxidative environment (52-53). In addition, DJ-1 can act as a redox-dependent molecular chaperone to inhibit α-synuclein aggregate formation (54-55). The present inventors have shown that DJ-1 can increase glutathione synthesis after oxidative stress and can upregulate heat shock protein 70 (Hsp70) to block α-synuclein aggregation (31). While the majority of PD patients do not carry DJ-1 gene mutations, results disclosed herein indicate that increasing DJ-1 expression to supra-normal levels can make dopamine neurons resistant to neurotoxic insults. Drugs that enhance DJ-1 gene expression may be neuroprotective for all Parkinson's disease patients.

Phenylbutyrate has additional metabolic effects. It can be a chaperone molecule. As a chemical chaperone, phenylbutyrate can bind and mask surface-exposed hydrophobic segments of unfolded proteins and thereby stabilize protein structure in the native conformation, reducing endoplasmic reticulum (ER) stress (56-58). In α-synuclein transgenic mouse model, it is possible that phenylbutyrate directly stabilizes mutant α-synuclein and prevents the formation of high molecular weight oligomers and fibrils.

As disclosed herein, the present inventors have found that increased expression of DJ-1 prevents progression of motor and cognitive complications in a transgenic mouse model of diffuse Lewy body disease. Accordingly, various neurodegenerative diseases can be treated by administering a compound that increases expression of DJ-1. For example, phenylbutyrate can increase DJ-1 expression and prevent progression of disease in patients with idiopathic Parkinson's or diffuse Lewy body disease.

REFERENCES

1. Cookson et al., (2010) Hum Mol Genet 19(R1), R21-27
2. Huang et al. (2004) Brain Res Brain Res Rev 46(1), 44-70
3. Allam et al., (2005) Neurol Res 27(2), 206-208
4. Brown et al., (2005) Environ Health Perspect., 113(9), 1250-1256
5. Morris, (2005) Ann Med 37(2), 86-96
6. Bonifati, (2005) Minerva Med 96(3), 175-186
7. Cookson, (2005) Annu Rev Biochem 74, 29-52
8. Polymeropoulos et al., (1997) Science 276(5321), 2045-2047
9. Kruger et al., (1998) Nat Genet 18(2), 106-108
10. Zarranz et al., (2004) Ann Neurol 55(2), 164-173
11. Spillantini et al., (1997) Nature 388(6645), 839-840
12. Baba et al., (1998) Am J Pathol 152(4), 879-884
13. Trojanowski et al., (1998) Arch Neurol 55(2), 151-152
14. Conway et al., (1998) Nat Med 4(11), 1318-1320
15. Hashimoto et al., (2003) Ann N Y Acad Sci 991, 171-188

16. Narhi et al., (1999) J Biol Chem 274(14), 9843-9846
17. Wood et al., (1999) J Biol Chem 274(28), 19509-19512
18. Zhou et al., (2000) Brain Res 866(1-2), 33-43
19. Alves Da Costa et al., (2002) J Biol Chem 277(52), 50980-50984
20. Zhou et al., (2002) Brain Res 926(1-2), 42-50
21. Kaul et al., (2005) Brain Res. Mol Brain Res 139(1), 137-152
22. Kim et al., (2005) Proc Natl Acad Sci USA 102(14), 5215-5220
23. Bonifati et al., (2003) Science 299(5604), 256-259
24. Hague et al., (2003) Ann Neurol 54(2), 271-274
25. Ibanez et al., (2003) Neurology 61(10), 1429-1431
26. Clark et al., (2004) Mov Disord 19(7), 796-800
27. Taira et al., (2004) EMBO Rep 5(2), 213-218
28. Canet-Aviles et al., (2004) Proc Natl Acad Sci USA 101(24), 9103-9108
29. Junn et al., (2009) J Neurosci Res 87(1), 123-129
30. Clements et al., (2006) Proc Natl Acad Sci USA 103(41), 15091-15096
31. Zhou et al., (2005) J. Biol. Chem. 280(52), 43150-43158
32. Ying et al., (2006) J Biol Chem 281(18), 12580-12586
33. Gardian et al., (2005) J Biol Chem 280(1), 556-563
34. Minamiyama et al., (2004) Hum Mol Genet 13(11), 1183-1192
35. Gardian et al., (2004) Neuromolecular Med 5(3), 235-241
36. Zhou et al., (2008) J Biol Chem 283(15), 9863-9870
37. Adams et al., (1996) Neurochem Res 21(5), 619-627
38. Zhou et al., (2004) J Biol Chem 279(11), 10128-10135
39. Hogarth et al., (2007) Mov Disord 22(13), 1962-1964
40. Brahe et al., (2005) Eur J Hum Genet 13(2), 256-259
41. Andreassi et al., (2004) Eur J Hum Genet 12(1), 59-65
42. Cudkowicz et al., (2008) Amyotroph Lateral Scler, 1-8
43. Tremolizzo et al., (2005) Amyotroph Lateral Scler Other Motor Neuron Disord 6(3), 185-186
44. Inden et al., (2007) J Neurochem 101(6), 1491-1504
45. Ono et al., (2009) Parkinsonism Relat Disord 15(9), 649-654
46. Ryu et al., (2005) J Neurochem 93(5), 1087-1098
47. Gondcaille et al., (2005) J Cell Biol 169(1), 93-104
48. Kim et al., (2006) Biochem Biophys Res Commun 342(4), 1168-1173
49. Yokota et al., (2004) Oncogene 23(31), 5340-5349
50. Kim et al., (2004) Carcinogenesis 25(10), 1813-1820
51. Taira et al., (2001) Gene 263(1-2), 285-292
52. Thomas et al., (2010) Hum Mol Genet
53. Irrcher et al., (2010) Hum Mol Genet 19(19), 3734-3746
54. Shendelman et al., (2004) PLoS Biol 2(11), e362
55. Zhou et al., (2006) J Mol Biol 356(4), 1036-1048
56. Yam et al., (2007) Invest Ophthalmol Vis Sci 48(4), 1683-1690
57. Perlmutter, (2002) Pediatr Res 52(6), 832-836
58. Papp et al., (2006) Handb Exp Pharmacol (172), 405-416

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for treating a neurodegenerative disease in a subject in need thereof, said method comprising administering to the subject a composition comprising glycerol phenylbutyrate, wherein the neurodegenerative disease is Parkinson's disease.

2. The method of claim 1, wherein administration of said composition increases DJ-1 protein expression by at least 50%.

3. The method of claim 1, wherein administration of said composition increases DJ-1 protein expression by at least 100%.

4. A method for treating a neurodegenerative disease in a subject in need of such a treatment, said method comprising increasing DJ-1 expression in said subject by administering a therapeutically effective amount of glycerol phenylbutyrate, wherein increasing DJ-1 expression reduces neuron death.

* * * * *